US00PP31858P2

(12) United States Plant Patent
Egger

(10) Patent No.: US PP31,858 P2
(45) Date of Patent: Jun. 9, 2020

(54) ***HEUCHERA* PLANT NAMED 'DARK NIGHT'**

(50) Latin Name: ***Heuchera* hybrid**
Varietal Denomination: Dark Night

(71) Applicant: Terra Nova Nurseries, Inc., Canby, OR (US)

(72) Inventor: Janet N. Egger, Seattle, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/501,733

(22) Filed: May 28, 2019

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ..... A01H 6/80
See application file for complete search history.

(56) References Cited

PUBLICATIONS

Trademark to 'Dark Knight' (Abandoned), serial No. 86236792, filed Mar. 31, 2014.*

* cited by examiner

*Primary Examiner* — Anne Marie Grunberg
(74) *Attorney, Agent, or Firm* — Klarquist Sparkman, LLP

(57) ABSTRACT

A new and distinct *Heuchera* plant characterized by black to dark purple colored leaves, lightly lobed and ruffled leaves, small, purplish pink flowers on medium tall spikes, good sun tolerance, a medium, low mounding habit with excellent crown count, and excellent vigor.

1 Drawing Sheet

Botanical denomination: *Heuchera* hybrid.
Variety designation: 'Dark Night'.
Trademark designation: SIRENS' SONG™ 'Dark Night'.
Cross reference to *Heuchera* 'Dark 'N' Bright', applied for concurrently having application Ser. No. 16/501,734.
Cross reference to *Heuchera* 'Orange Delight', applied for concurrently having application Ser. No. 16/501,732.

BACKGROUND OF THE INVENTION

The present invention relates to a new and distinct cultivar of *Heuchera* given the cultivar name of 'Dark Night'. *Heuchera* is in the family Saxifragaceae. *Heuchera* 'Dark Night' originated as a controlled cross using *Heuchera* 'B122-9', a proprietary, unpatented, unnamed plant as the seed parent, and *Heuchera* 'B110-5', a proprietary plant as the pollen parent. These parents are a result of breeding plan to produce purple-leaved *Heuchera* with good crowns.

Compared to the seed parent, *Heuchera* 'B122-9', the new cultivar has purplish pink rather than hot pink flowers.

Compared to the pollen parent, *Heuchera* 'B110-5', the new cultivar has taller flower peduncles and more crowns.

Compared to *Heuchera* 'Obsidian', U.S. Plant Pat. No. 14,836, the new cultivar has more crowns, and purplish pink flowers rather than yellow green.

Compared to *Heuchera* 'TNHEUNEB', U.S. Plant Pat. No. 30,583, the new cultivar is smaller in size, and has solid purplish pink flowers rather than bi-colored pink and white flowers.

*Heuchera* 'Dark Night' is uniquely distinguished by:

1. black to dark purple colored leaves,
2. lightly lobed and ruffled leaves,
3. small, purplish pink flowers on medium tall spikes, 4. good sun tolerance,
5. a medium small, low mounding habit with excellent crown count, and
6. excellent vigor.

This new cultivar has been reproduced only by asexual propagation (tip cuttings and tissue culture using growing tips). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
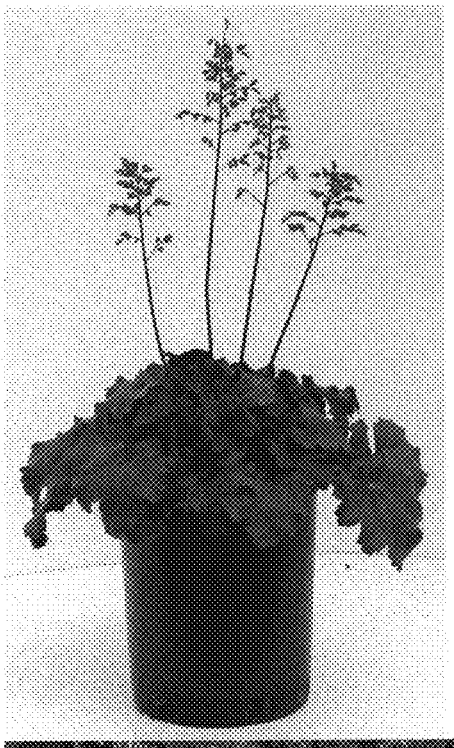
FIG. 1 shows a nine-month-old plant of *Heuchera* 'Dark Night' growing in a one-gallon pot in a temperature controlled greenhouse in February in Canby, Oreg.
Figure 2:
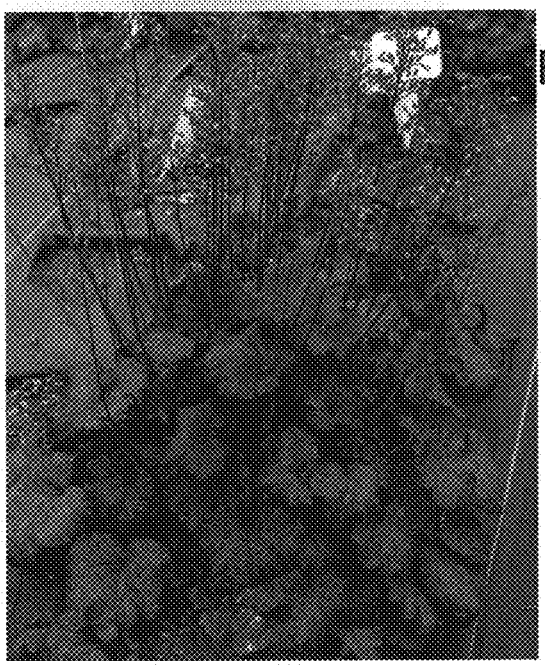
FIG. 2 shows a one-year-old plant of *Heuchera* 'Dark Night' growing in the trial bed in part sun in late April in Canby, Oreg.

The following is a detailed description of the new *Heuchera* cultivar based on observations taken in September of an eight-month-old specimen growing in a one-gallon pot in partial shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5th edition, 2007.

Plant:

*Form.*—Basal rosette, herbaceous perennial.
*Hardiness.*—USDA Zone 4 to 9.
*Size.*—14 cm tall from top of the foliage to the ground, 33 cm from ground to top of flowers, 32 cm wide.
*Number of crowns.*—About 15.
*Habit.*—Medium small, low mound.
*Vigor.*—Excellent.

Leaf:

*Type.*—Simple.
*Arrangement.*—Rosette.
*Shape.*—Widely depressed ovate.
*Number.*—About 50.
*Blade size.*—Grows to 9 cm long and 9.5 cm wide.
*Venation.*—Palmate.
*Lobing/Division.*—Palmately lobed with 5 main lobes with secondary lobes.
*Undulation.*—Weak.
*Glossiness.*—Medium.
*Margins.*—Crenate and undulate.
*Apex.*—Mucronulate.
*Base.*—Cordate.
*Surface texture.*—Glandular-puberulent on both sides.
*Leaf rugosity.*—Medium.
*Petiole description.*—Grows to 11 cm long and 3 mm wide, glandular hairs, Greyed Purple N186C.
*Leaf color.*—Topside between Greyed Purple N186C and Greyed Purple N186A including veins, bottom side between Greyed Purple N187A and Greyed Purple 187B.

Inflorescence:

*Size.*—Grows to 7 cm wide and 16 cm long.
*Type.*—Upright thyrse.
*Number of flowers per thyrse.*—About 60.
*Flower density.*—Moderate to light.
*Number of thyrse.*—Up to 40.
*Peduncle.*—Grows to 20 cm long and 3 mm wide at base, glandular hairs, between Black 203A and Greyed Purple 187A.
*Flowering stem attitude.*—Upright.
*Pedicel.*—Grows to 3 mm long, with glandular hairs, between Black 203A and Greyed Purple 187A.
*Bloom period.*—July to frost in Canby, Oreg.

Flower bud:

*Size.*—4 mm wide and 5 mm long.
*Description.*—Glandular-puberulent, ovoid, horizontal to down facing.
*Color.*—Red Purple 64B.

Flower:

*Type.*—Perfect.
*Shape.*—Campanulate.
*Attitude.*—Side-facing.
*Size.*—6 mm long and 5 mm wide.
*Corolla description.*—5 petals, each 2 mm long and 1mm wide, spatulate, margins entire, tip acute, glabrous on topside, glandular-puberulent on bottom side, both sides Red Purple 64B.
*Calyx description.*—Campanulate, 5 mm long and 4 mm wide, with 5 lobes with wide sinuses divided ½ way to the base, each 2 mm wide and 3 mm long, oblong in shape, back side glandular-puberulent with glandular hairs, glabrous inside, tip obtuse, margin entire, outside Red Purple 64B inside Red Purple 64B.
*Stamen description.*—5 in number, filaments 2 mm long, White NN155C, anthers 0.5 mm long, Yellow Orange 22A, pollen absent.
*Pistil description.*—1, 2-beaked, 5 mm long and 2 mm wide, Red Purple 61C overall, ovary 2 mm long and 2 mm wide, style 3 mm long.
*Lastingness.*—Each thyrse blooms for about 3 weeks on the plant.

Fruit:

*Type.*—Two-beaked ovoid capsule.
*Fertility.*—Moderate.
*Color.*—Greyed Brown 199C.

Seed:

*Shape.*—Linear.
*Size.*—2 mm long.
*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *